United States Patent
Ponomarev et al.

(10) Patent No.: US 8,896,073 B2
(45) Date of Patent: Nov. 25, 2014

(54) INTEGRATED CIRCUIT AND MANUFACTURING METHOD

(71) Applicant: NXP B.V., Eindhoven (NL)

(72) Inventors: Youri Victorovitch Ponomarev, Lueven (BE); David Tio Castro, Oud Heverlee (BE); Roel Daamen, Herkenbosch (NL)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 13/745,918

(22) Filed: Jan. 21, 2013

(65) Prior Publication Data
US 2013/0193417 A1  Aug. 1, 2013

(30) Foreign Application Priority Data
Jan. 31, 2012  (EP) .................................... 12153390

(51) Int. Cl.
| | | |
|---|---|---|
| H01L 27/14 | (2006.01) | |
| G01N 27/22 | (2006.01) | |
| H01L 51/42 | (2006.01) | |
| H01L 51/00 | (2006.01) | |
| G01N 27/12 | (2006.01) | |

(52) U.S. Cl.
CPC .............. H01L 51/42 (2013.01); G01N 27/223 (2013.01); H01L 51/0034 (2013.01); G01N 27/121 (2013.01)
USPC ........................................... 257/414; 438/49

(58) Field of Classification Search
None
See application file for complete search history.

(56) References Cited

U.S. PATENT DOCUMENTS

| | | | |
|---|---|---|---|
| 5,130,776 A | 7/1992 | Popovic et al. | |
| 6,396,040 B1 | 5/2002 | Hill | |
| 6,504,142 B2 | 1/2003 | Nixon et al. | |
| 6,507,286 B2 | 1/2003 | Weindorf et al. | |
| 6,541,777 B1 | 4/2003 | Lombardo et al. | |
| 6,583,880 B2 | 6/2003 | Berstis | |
| 6,596,981 B1 | 7/2003 | Aswell et al. | |
| 6,831,344 B2 | 12/2004 | Ogawa et al. | |
| 7,214,922 B2 | 5/2007 | Takiba et al. | |
| 7,235,765 B2 | 6/2007 | Clugston, Jr. | |
| 7,538,406 B2 | 5/2009 | Lin et al. | |
| 7,663,313 B2 * | 2/2010 | Park .............................. | 313/512 |
| 7,755,117 B2 | 7/2010 | Kalnitsky et al. | |
| 7,759,626 B2 | 7/2010 | Kikuchi et al. | |
| 2002/0053635 A1 | 5/2002 | Schroter et al. | |

(Continued)

FOREIGN PATENT DOCUMENTS

| | | |
|---|---|---|
| EP | 2 505 978 A1 | 10/2012 |
| JP | 2008 211124 A | 9/2008 |
| WO | 2010/068653 A2 | 6/2010 |

OTHER PUBLICATIONS

Extended European Search Report for Application No. 12153390.5 (Jun. 14, 2012).

*Primary Examiner* — Sonya D McCall Shepard

(57) ABSTRACT

Disclosed is an integrated circuit comprising a substrate including at least one light sensor; an interconnect structure over the substrate; at least one passivation layer over the interconnect structure, said passivation layer including a first area over the at least one light sensor; and a gas sensor such as a moisture sensor at least partially on a further area of the at least one passivation layer, wherein the gas sensor comprises a gas sensitive layer in between a first electrode and a second electrode, the gas sensitive layer further comprising a portion over the first area. A method of manufacturing such an IC is also disclosed.

12 Claims, 3 Drawing Sheets

(56) References Cited

U.S. PATENT DOCUMENTS

Figure 1:
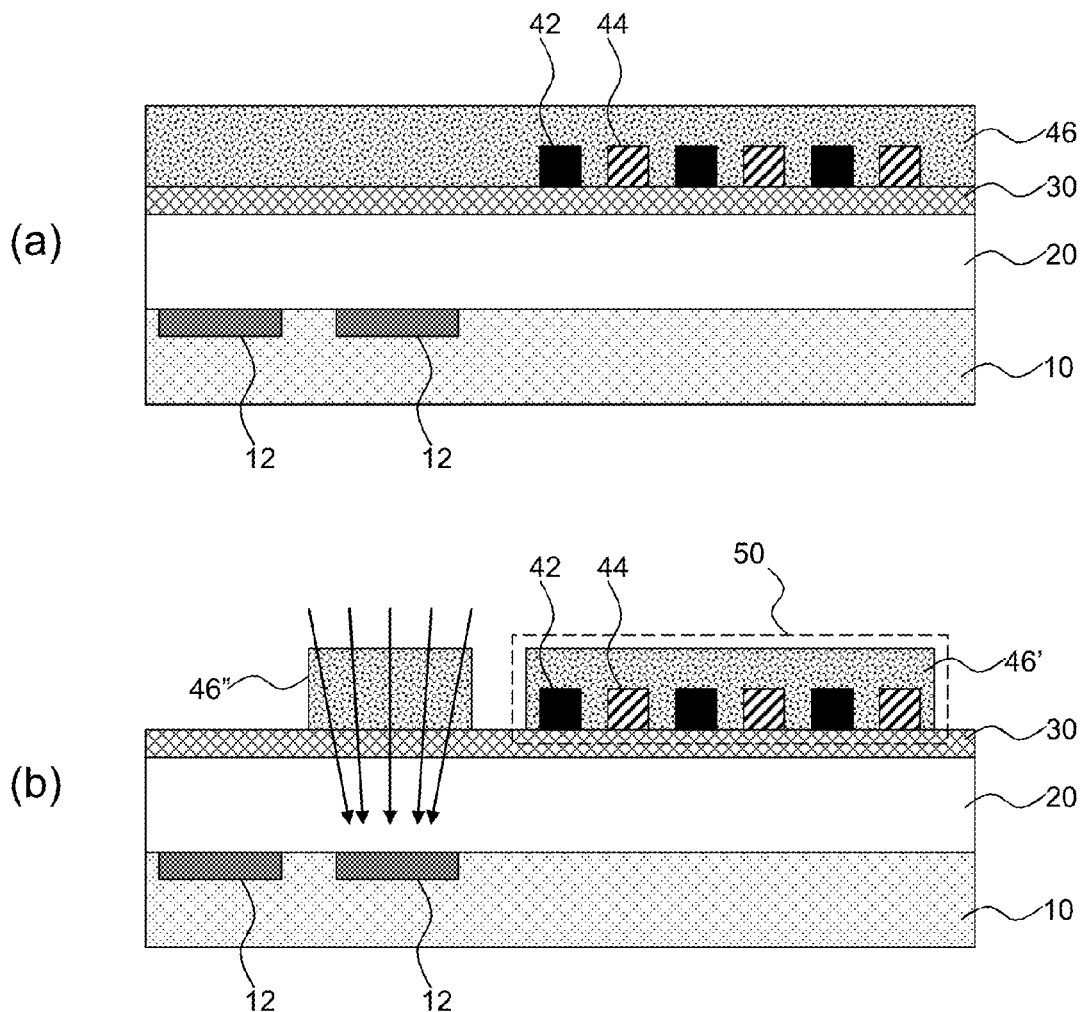

| | | |
|---|---|---|
| 2003/0132369 A1 | 7/2003 | Aswel et al. |
| 2005/0218465 A1* | 10/2005 | Cummins ............... 257/414 |
| 2008/0173796 A1 | 7/2008 | Lum et al. |
| 2010/0072351 A1 | 3/2010 | Mahowald |
| 2010/0102230 A1 | 4/2010 | Chang et al. |
| 2010/0163717 A1 | 7/2010 | Chang et al. |
| 2010/0282953 A1 | 11/2010 | Tam |
| 2010/0283998 A1 | 11/2010 | Souchkov et al. |
| 2010/0294024 A1 | 11/2010 | Kumar et al. |
| 2010/0300856 A1 | 12/2010 | Pance et al. |
| 2011/0045600 A1* | 2/2011 | Ren et al. ............... 436/133 |
| 2011/0185810 A1 | 8/2011 | Humbert et al. |
| 2012/0211845 A1 | 8/2012 | Daamen et al. |

* cited by examiner

INTEGRATED CIRCUIT AND MANUFACTURING METHOD

CROSS-REFERENCE TO RELATED APPLICATIONS

This application claims the priority under 35 U.S.C. §119 of European patent application no. 12153390.5, filed on Jan. 31, 2012, the contents of which are incorporated by reference herein.

FIELD OF THE INVENTION

The present invention relates to an integrated circuit (IC) comprising a substrate including at least one light sensor; an interconnect structure over the substrate and at least one passivation layer over the interconnect structure.

The present invention further relates to a method of manufacturing such an IC.

BACKGROUND OF THE INVENTION

In a number of applications ranging from automotive to home automation and mobile computing, information retrieval on the amount of ambient light, e.g. in the photopic range of the electromagnetic spectrum, (i.e. light visible to the human eye) can be commercially interesting. Such information can for instance be used to control the light sources in an environment such that an appropriate tradeoff between comfortable lighting levels and energy consumption is established, to adjust the brightness of a mobile device display to prolong battery operating time, engage the headlights of a vehicle, e.g. when entering a tunnel, and so on.

In addition to photopic information, detection of UV and IR irradiation levels can also be of interest to either distinguish the type of the ambient light conditions, e.g. artificial light versus sunlight, or to deliver complete information on the environment's comfort level, such as the inclusion of information on UV exposure and the presence of radiant heat sources.

Photo-sensitive Si diodes may be used as light sensing elements. The light is absorbed in Si substrate by generating electron-hole pairs near the depletion region of a typically reversed-biased $n^+/p$ (or $p^+/n$) diodes, these carriers are separated by the depletion region and as a result generate photo-current that can be measured. The photocurrent is directly proportional to the light intensity; hence these devices can be used as light sensor transducers.

Si diodes in general have little wavelength selectivity and detect a rather wide spectrum that can include UV, visible as well as IR irradiation up to 1100 nm. Significant amount of literature exists on how it is possible to vary the sensitivity of the photodiodes to a given part of the spectrum using different diffusion depths of the dopants to form the diode junctions, formation of vertically-stacked diodes, as well as package- or casing-level filters applications. These methods, however, either do not deliver appropriate selectivity to the various parts of the spectrum and require a significant amount of signal post-processing, or only allow a single part of the spectrum to be sensed by each ALS (ambient light sensor) device.

With the ongoing diversification of electronic devices or electronic information gathering such as by RF tags on packaged articles, it is often desirable to include different types of sensors in a single IC. For instance, the detection of other environmental parameters, for instance temperature and humidity such as for HVAC (heating, ventilation and air conditioning) control in buildings and cars, could be particularly desirable.

Such multiple sensor ICs are known per se. However, most solutions are based on a system comprising multiple discrete sensors, which makes the system bulky and rather expensive. Also, the manufacturing process can be rather complex, especially when multiple light sensors for detecting different parts of the EM spectrum are to be integrated into a single IC. This negatively impacts on production yield and pushes up the price of the known good products.

US2005/0218465 A1 describes a single chip wireless sensor that comprises a microcontroller connected by a transmit/receive interface to a wireless antenna. The device senses humidity and temperature, and a humidity sensor is connected by an 18 bit SigmaDelta A-to-D converter to the microcontroller and a temperature sensor is connected by a 12 bit SAR A-to-D converter to the microcontroller. The device is an integrated chip manufactured in a single process in which both the electronics and sensor components are manufactured using standard CMOS processing techniques.

JP 2008 211124 A describes providing a means which prevents a liquid-like sealing resin from flowing out without functionally damaging an upper exposed surface wherein a sensor and an MEMS are formed by performing resin sealing for only an electrical connection part of the upper exposed surface of a semiconductor chip.

SUMMARY OF THE INVENTION

The present invention seeks to provide a compact IC comprising at least one light sensor and a moisture sensor such as a relative humidity sensor.

The present invention further seeks to provide a method for manufacturing such an IC in a cost-effective manner.

According to an aspect of the present invention, there is provided an integrated circuit comprising a substrate including at least one light sensor; an interconnect structure over the substrate; at least one passivation layer over the interconnect structure, said passivation layer including a first area over the at least one light sensor; and a gas sensor at least partially on a further area of the at least one passivation layer, wherein the gas sensor comprises a gas sensitive layer in between a first electrode and a second electrode, the gas sensitive layer further comprising a portion over the first area.

The present invention has been based on the insight that gas sensitive materials such as materials that exhibit a dielectric constant that is dependent on the gas, e.g. CO, $CO_2$ and/or moisture, levels in the material can also be used as light filters for a light sensor such as a photosensitive diode in the substrate by positioning a portion of the gas sensitive materials on an area of the passivation stack over the light sensor, thereby effectively using the absorption spectrum of the gas sensitive material as the filtering properties of the filter material. As the gas sensitive material is also used as filter for a part of the EM spectrum, the IC can be more compact and is more cost-effective as only a single processing step is required, i.e. the deposition of the gas sensitive material to form both the gas sensor, e.g. a moisture sensor such as a relative humidity sensor, and the filter of the photosensitive element, i.e. the light sensor, in the substrate underlying the portion of the gas sensitive material acting as filter.

In an embodiment, the moisture sensitive layer is a polymer layer, in which the polymer preferably is selected from the group consisting of polyacrylates, polymethacrylates, polyimides, polyamides, polyamines, polypyridines, polycarbonates, polyacetates and polystyrenes and derivatives thereof as such polymers are known to have dielectric constants and/or conductive properties that depend on the amount of moisture absorbed by the polymer. Polyimide is a particularly preferred polymer as this polymer exhibits a particularly large dependence of its dielectric constant to the moisture levels in the polymer, as for instance has been disclosed by M. Dokmecki in the Journal of Microelectromechanical Systems, 2001, Vol. 10, pages 197-204, and has optical properties that can be tuned by controlling its curing temperature as for instance has been disclosed in J. Chem. Phys., 1993, Vol. 38, page 3445.

Alternatively, polymers such as polyacetylenes, polyanilines, polypyrroles, polythiophenes, poly(phenyl vinylene) and derivatives thereof may be used, in particular if gases other than gaseous water (moisture) are to be detected. The absorption properties of the gas sensitive material such as a suitable polymer may be tuned by the inclusion of a dye in the material. Such a dye may be dissolved or otherwise dispersed through the gas sensitive material, or may be chemically bound to the gas sensitive material, e.g. by covalent, ionic or VanderWaals bonding of the dye to a suitable polymer. As only small amounts of dye need adding, the gas, e.g. moisture, sensitivity of the material remains substantially unaltered. For this reason, any suitable dye may be used as the only consideration is the desired absorption spectrum of the selected dye, which is well-documented for numerous dyes, such that it is practically unfeasible to include particular examples of such dyes in the present application.

In an embodiment, the IC may comprise more than one photosensitive element, for some of which the area of the passivation stack over such an additional light sensor may remain uncovered, thus providing multiple light sensors that are sensitive to different parts of the EM spectrum. Alternatively, the area of the of the passivation stack over such an additional light sensor may be covered by a further portion of the gas sensitive material, which for instance may have been impregnated with a further dye to distinguish its filtering properties from the portion of the gas sensitive material in the first area.

The IC of the present invention may be suitably integrated in devices such as electronic devices, vehicles and so on, as well as in packaged items, in which case the IC may for instance be a RF-ID chip for monitoring environmental conditions of the packaged item, which monitoring data may be relayed to a control center via the RF link.

According to another aspect of the present invention, there is provided a method of manufacturing an integrated circuit comprising at least one light sensor and a gas sensor such as a moisture sensor, the method comprising providing a substrate including at least one light sensor; forming an interconnect structure over the substrate; forming at least one passivation layer over the interconnect structure, said passivation layer including a first area over the at least one light sensor; forming a gas sensor at least partially on the at least one passivation layer by forming a pair of electrodes on a further area of the at least one passivation layer; depositing a gas sensitive layer over the at least one passivation layer including the pair of electrodes; and patterning the gas sensitive layer such that the gas sensitive layer remains in the first and further areas Because the patterning of the gas sensitive layer is usually necessary anyway, the insight of the present invention that one or more filters of parts of the EM spectrum can be provided by also using the gas sensitive layer material for this purpose means that such filters can be provided in the same patterning step, such that the inclusion of such filters is provided without adding to the complexity of the manufacturing process, i.e. without requiring additional processing steps, which renders the method of the present invention particularly cost effective whilst at the same time not negatively affecting production yield.

A dye may be included in at least the portion of the gas sensitive layer over the first area to tune the properties of the filter. Such a dye may be chemically bound to the moisture sensitive layer material, e.g. covalently bound, ionically bound or bound by VanderWaals forces.

In case the gas sensitive layer material is a polymer layer is selected from the group consisting of polyacrylates, polymethacrylates, polyimides, polyamides, polyamines, polypyridines, polycarbonates, polyacetates and polystyrenes, polyacetylenes, polyanilines, polypyrroles, polythiophenes, poly(phenyl vinylene) and derivatives thereof, wherein the step of depositing a moisture sensitive layer may be achieved by spin-coating.

BRIEF DESCRIPTION OF THE EMBODIMENTS

Figure 2:
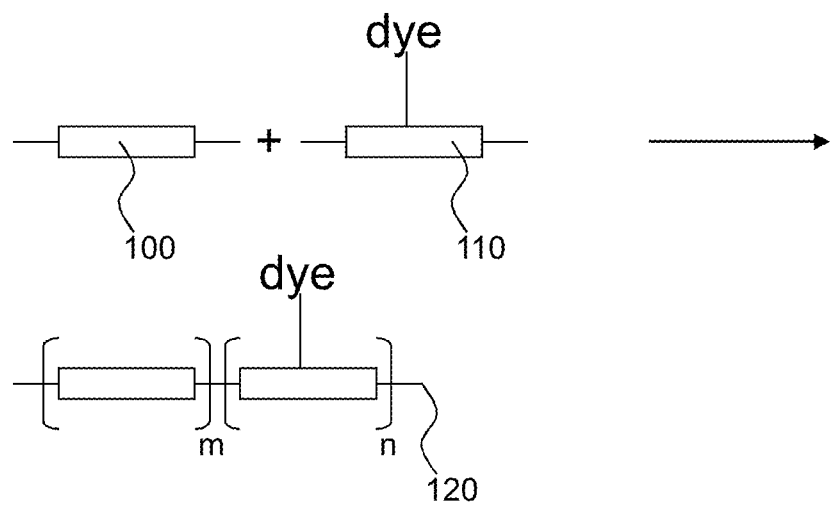
Figure 3:
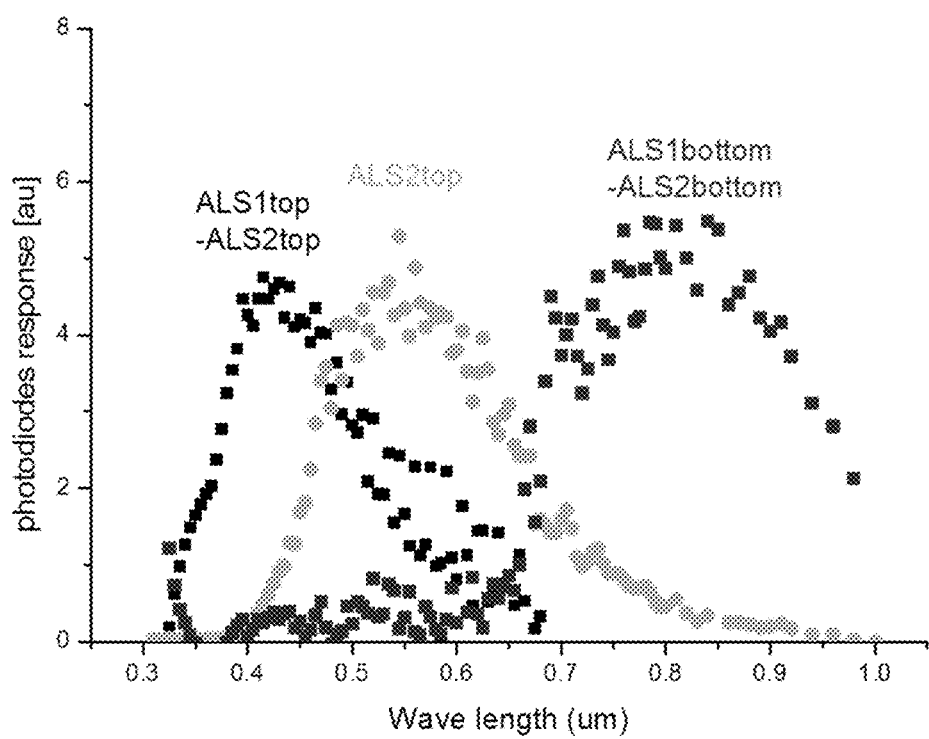
Figure 4:
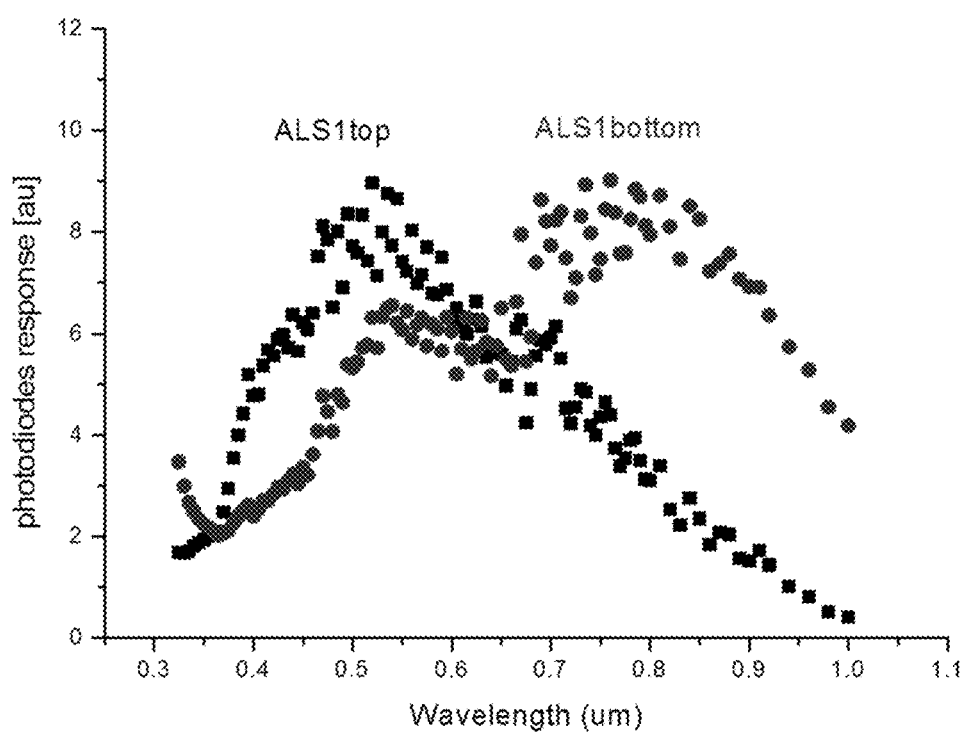

Embodiments of the invention are described in more detail and by way of non-limiting examples with reference to the accompanying drawings, wherein:

FIG. 1 schematically depicts an IC manufacturing method according to an embodiment of the present invention;

FIG. 2 schematically depicts a reaction scheme that may be used in an embodiment of the present invention;

FIG. 3 depicts a measurement result of an IC according to an embodiment of the present invention; and FIG. 4 depicts another measurement result of an IC according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts a method of manufacturing an IC in accordance with an embodiment of the present invention. The IC of the present invention may be provided using any suitable manufacturing technology, such as CMOS, silicon-on-insulator and SiGe technologies. As shown in FIG. 1(a), there is provided an IC that comprises a substrate 10, e.g. a Si substrate, a SiGe substrate, a silicon on insulator (SOI) substrate and so on, which typically comprises a plurality of circuit elements such as transistors, diodes, and so on, combinations of which from circuits. These may be analog or digital circuits. The manner in which this substrate provided is not particularly limited.

Any suitable manufacturing method may be employed to provide such a substrate. As such methods are numerous and commonplace, this will not be further explained for the sake of brevity only. It should further be understood that the present invention is not limited to specific types of ICs. The present invention may be included in any suitable IC, including digital ICs, analog ICs and mixed signal ICs.

A number of photosensitive elements 12 formed on the substrate 10 are explicitly shown. The photosensitive elements 12 may take any suitable shape, e.g. photosensitive diodes, which may be single diodes, vertically stacked diodes and so on. In case of a vertically stacked diode, the substrate 10 is usually at least partially transparent such that the bottom diode can be illuminated through the substrate. This may for instance be achieved by thinning the substrate to a thickness such that it becomes as at least partially transparent. The photosensitive elements 12 are typically connected to be used as light sensors in the IC.

The interconnections between the circuit elements in the substrate 10 to define the circuits are typically provided by a metallization layer or layer stack 20, which by way of non-limiting example may comprise a plurality of patterned metal layers separated by dielectric layers. Any suitable number of metal layers and dielectric layers may be present. Metal portions in different metal layers may be conductively interconnected by one or more vias formed in a dielectric layer in between the respective portions of the metal layers. Any suitable material may be used to form the metallization stack 20, such as Ti, TiN, Al, Cu and combinations thereof to define the metal layers and silicon oxide, silicon nitride, low-k dielectrics and other dielectric materials as well as combinations thereof to form the dielectric layers.

Each layer of the metallization stack 20 may in fact comprise a stack of layers, as is common design practice in contemporary semiconductor technologies such as sub-micron CMOS technologies. Any suitable manufacturing method may be employed to provide such an interconnect structure. As such methods are numerous and commonplace, this will not be further explained for the sake of brevity only.

A passivation layer 30 is typically provided over the metallization stack 20 to protect the interconnect structure and the substrate 10 from damage, e.g. from exposure to excess moisture. Again, any suitable passivation layer 30 may be employed. Non-limiting examples of suitable materials for such a passivation structure include dielectric materials such as $SiO_2$, $Si_3N_4$, low-k dielectrics and combinations thereof. In addition, the passivation structure may further comprise a moisture barrier material such $Ta_2O_5$. Preferably, the passivation layer 30 is a layer stack comprising one or more layers of a dielectric material, which may be formed in any suitable manner. As such methods are numerous and commonplace, this will not be further explained for the sake of brevity only.

It will be clear that the metallization layer 20 and the passivation layer 30 are at least partially transparent to the part of the electromagnetic (EM) spectrum of interest, such that this light can reach the photosensitive element 12.

A first electrode 42 and a second electrode 44 are formed on top of the passivation layer 30, which preferably is planarized prior to the formation of these electrodes. A suitable planarization method is chemical mechanical polishing. The electrodes 42 and 44 may be formed in any suitable manner, e.g. by depositing a metal layer on top of the passivation layer 30 and patterning this metal layer to obtain the first electrode 42 and the second electrode 44. In FIG. 1(a), the first electrode 42 and the second electrode 44 are shown as interdigitated electrodes by way of non-limiting example only. It will be appreciated that any suitable electrode design may be contemplated. Any suitable metal may be used for the electrodes. Preferably, the first electrode 42 and the second electrode 44 are formed of a metal that is also used to form the metal interconnects in the metallization layer 20 as this means that the electrodes may be formed by processes that are already available in the manufacturing process of the IC.

The electrodes 42 and 44 form the electrodes of a gas sensor such as a moisture sensor formed on top of the passivation layer of the IC. A non-limiting example of such a type of sensor is described in more detail in European patent application EP09166518.2. The electrodes 42 and 44 may be conductively connected for reading out purposes in any suitable manner. The electrodes 42 and 44 may be connected to circuitry on the substrate of the IC via the metallization stack 20, in which case respective electrically conductive portions extend from the electrodes 42 and 44 to different metal portions of the metallization stack 20 through the passivation layer 30. Alternatively, the passivation layer 30 may carry respective contact pads (not shown) to which the electrodes 42 and 44 are conductively connected such that the gas sensor may be read out externally by contacting these contact pads.

According to an embodiment of the present invention, a gas sensitive layer 46 is formed over the passivation layer 20 including the first electrode 42 and the second electrode 44. In the context of the present invention, a gas sensitive material is a material that has electrical properties, e.g. conductive, resistive and/or capacitive properties that are a function of the gas content in the material. For instance, in case of a capacitive moisture sensor, the moisture sensitive material is a material that has a dielectric constant that depends on its moisture content, such that the moisture content can be determined by determining the capacitance of the sensor.

Alternatively, an impedance measurement across the portion of the liquid retention layer 46 in between the electrodes 42 and 44 can be performed to determine the relative humidity of the environment in which the IC is placed. Such a measurement could also be used to determine if the IC has been exposed to excessive humidity levels, e.g. has been immersed in water.

It will be understood that in case of the gas sensor being a moisture sensor on the passivation layer 30, this sensor may be used as a relative humidity sensor or as a liquid immersion sensor instead.

Any suitable moisture sensitive material may be used. For example, the moisture sensitive material may be a polymer selected from the group consisting of polyacrylates, polymethacrylates, polyimides, polyamides, polyamines, polypyridines, polycarbonates, polyacetates and polystyrenes and derivatives thereof. Polyimide is particularly preferred. In case of the layer 46 comprising such a polymer, the layer 46 may for instance be formed by spin-coating or any other suitable polymer deposition technique.

Alternatively, polymers such as polyacetylenes, polyanilines, polypyrroles, polythiophenes, poly(phenyl vinylene) and derivatives thereof may be used, in particular if gases other than gaseous water (moisture) are to be detected. It is for instance known per se that several conductive polymers such as polypyrrole, polyaniline, polythiophene and their derivatives have successfully been used as gas sensitive layers in gas sensors. It is also known per se that for instance polythiophene and poly(dodecylthiophene) sensors can have sensitivities in the range of 0.2-1.8 DR/Rb for 300 ppm gas for 10 minutes for gases such as methane, chloromethane and ammonia, as for instance has been previously disclosed by Y. Sakurai et al. in Sensors and Actuators B: Chemical, Vol. 83, No. 1-3, pages 270-275.

More generally, any suitable polymer may be used. An overview of some suitable polymers for use in gas sensors has been provided by Hua Bai et al. in Sensors 2007, Vol. 7, pages 267-307. Another overview of suitable polymers for gas sensor applications is provided by K. Arshak et al. in Sensor Review, 24(2), 2004, pages 181-198.

To enhance the gas sensitivity of the polymers, at least the portion of the gas sensitive layer 46 forming part of the gas sensor may be coated with a noble metal such as Pt or Pd. Alternatively, such a noble metal may be dispersed in the polymer. For the interested reader, this is disclosed in more detail in the aforementioned article by Hua Bai et al.; see in particular Table 2 of this article.

In a next step, as shown in FIG. 1(b), the layer 46 of the gas sensitive material is patterned to finalize the gas sensor 50 including a portion 46' of the gas sensitive material and to provide a further portion 46" that acts as a filter for one of the photosensitive elements 12. The portion 46' and the further portion 46" may still be interconnected or may be separated in the patterning step. The further portion 46" is located on an area of the passivation layer 30 over the photosensitive element 12 such that the majority of the incident light of the photosensitive element 12 as indicated by the arrows in FIG. 1(*b*) passes through the further portion 46". Preferably, substantially all incident light, e.g. at least 90% or even 99% of all incident light of the photosensitive element 12 passes through the portion 46" of the moisture sensitive material acting as the filter for this photosensitive element.

In an embodiment, the filter characteristics, i.e. the part of the incident electromagnetic (EM) spectrum absorbed by the portion 46", are governed by the absorption characteristics, i.e. the absorption spectrum of the gas sensitive material. To this end, the gas sensitive material may be selected based on the nature of its absorption spectrum to ensure that it can effectively filter out the undesirable part of the EM spectrum. For instance, for a photopic light sensor 12, a material may be selected that strongly absorbs UV and IR irradiation.

In a further embodiment, the absorption spectrum of at least the filter portion 46" of the gas sensitive material may be tuned by adding a dye to the portion 46". Due to the intense color of dyes, only a small amount of dye may need to be added to the gas sensitive material to alter its absorption spectrum. Any suitable dye may be used. The advantage of having to use only a small amount of dye is that the electrical properties of the gas sensitive material remain substantially unaffected. This means that the dye may also be present in the portion 46' forming part of the gas sensor 50, which may simplify application of the dye to the gas sensitive material.

For instance, the dye may be added after the layer 46 of the gas sensitive material has been deposited over the passivation layer 30, e.g. by absorption of the dye into the layer 46. Alternatively, in case of the gas sensitive material comprising a polymer, the dye may be incorporated into polymer. This may for instance be achieved by using two different types of monomers, i.e. a monomer 100 without the dye chemically, e.g. covalently, bound thereto and a monomer 110 comprising the dye, for instance as a substituent, as schematically depicted in FIG. 2, to form a polymer 120 in which the dye is incorporated as a substituent to the polymer backbone. In FIG. 2, m and n are positive integers, with m typically being much larger than n as excess monomer 100 compared to monomer 110 is used in the polymerization reaction. In an embodiment, the ratio of monomer 100:monomer 110 may be at least 10:1, and may be as large as 100:1 or even 1,000:1. As the chemistry of attaching a dye to a monomer is well-known and furthermore highly dependent on the nature of the dye as well as the monomer, this is not explained in further detail for the sake of brevity only.

FIG. 3 depicts the results of a measurement performed on a CMOS IC comprising a pair of vertically stacked photosensitive diodes labeled ALS1 and ALS2 in FIG. 3, in which only ALS2 is covered by a polyimide portion, i.e. the area of the passivation layer 20 over ALS2 comprises this portion. Three measurement curves are depicted in FIG. 3. The curve ALS1top-ALS2top depicts the differential spectrum obtained by subtracting the spectral response of the top diode of ALS2 from the spectral response of the top diode of ALS 1. The curve ALS2top depicts the spectral response of the top diode of ALS2 and the curve ALS1 bottom-ALS2bottom depicts the differential spectrum obtained by subtracting the spectral response of the bottom diode of ALS2 from the spectral response of the bottom diode of ALS 1.

As can be seen from curves ALS1top-ALS2top and ALS1bottom-ALS2bottom, a separation of the UV and IR parts of the EM spectrum can be achieved. This can be achieved by simple arithmetic manipulation of the ALS1 and ALS2 signals.

FIG. 4 depicts the spectral response of the (unfiltered) ALS1 top and bottom diode before applying the data extraction shown in FIG. 3. Compared to the response of the ALS2 top diode in FIG. 3 it will be clear that the UV and IR wings of the spectral response of the ALS1 top diode have been effectively suppressed by the polyimide filter portion over the ALS2 top diode.

It should furthermore be understood that other types of sensors may be added to the IC without departing from the teachings of the present invention. In particular, sensors that can be manufactured using process steps already in use for the manufacturing of the IC are preferred as they do not require a substantial cost increase of the manufacturing process to add such sensors to the IC. An example of a particularly preferable sensor is a temperature sensor such as a PTAT sensor, for which transistor-based implementations are readily available.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An integrated circuit comprising:
   a substrate including at least one light sensor;
   an interconnect structure over the substrate, the interconnect structure at least partially transparent to light such that light from outside the integrated circuit can reach the at least one light sensor;
   at least one passivation layer over the interconnect structure, said passivation layer including a first area over the at least one light sensor;
   and a gas sensor at least partially on a further area of the at least one passivation layer, wherein the gas sensor comprises a gas sensitive layer in between a first electrode and a second electrode, the gas sensitive layer further comprising a portion over the first area.

2. The integrated circuit of claim 1, wherein the gas sensor is operable to detect moisture.

3. The integrated circuit of claim 2, wherein the gas sensor is a relative humidity sensor.

4. The integrated circuit of claim 1, wherein the gas sensitive layer is a polymer layer.

5. The integrated circuit of claim 4, wherein the polymer layer is selected from the group consisting of polyacrylates, polymethacrylates, polyimides, polyamides, polyamines, polypyridines, polycarbonates, polyacetates, polystyrenes, polyacetylenes, polyanilines, polypyrroles, polythiophenes, poly(phenyl vinylene) and derivatives thereof.

6. The integrated circuit of claim 5, wherein the polymer is a polyimide.

7. The integrated circuit of claim 1, wherein the gas sensitive layer further comprises a dye in at least said portion.

8. The integrated circuit of any of claim 1, wherein the light sensor is a photosensitive diode.

9. The integrated circuit of any of claim 1, comprising a further light sensor in the substrate under an area of the at least one passivation layer uncovered by said portion.

10. The integrated circuit of claim 1, further comprising a temperature sensor.

11. A packaging article comprising the integrated circuit of claim 1.

12. An electronic device comprising the integrated circuit of claim 1.

* * * * *